United States Patent [19]
Thatcher

[11] 3,972,238
[45] Aug. 3, 1976

[54] PHYSICAL CONTACT TRAINING APPARATUS

[76] Inventor: Richard Eugene Thatcher, 10709 Lunswood Road, Chester, Va. 23831

[22] Filed: July 10, 1975

[21] Appl. No.: 594,698

[52] U.S. Cl................................. 73/380; 272/140; 273/55 R
[51] Int. Cl.² .......................................... G01L 5/02
[58] Field of Search............... 73/380; 273/1 R, 1 B, 273/55 R; 272/83 R, 79 R, 80, 81, 76; 244/151 R

[56] References Cited
UNITED STATES PATENTS

| | | | |
|---|---|---|---|
| 3,124,326 | 3/1964 | Bockelmann | 244/151 R |
| 3,519,269 | 7/1970 | Howlett | 273/55 |

FOREIGN PATENTS OR APPLICATIONS

| | | | |
|---|---|---|---|
| 465,908 | 9/1928 | Germany | 73/380 |
| 11,675 | 7/1892 | United Kingdom | 272/80 |

*Primary Examiner*—S. Clement Swisher
*Assistant Examiner*—Denis E. Corr
*Attorney, Agent, or Firm*—Norman B. Rainer

[57] ABSTRACT

A teaching, force measuring, and conditioning apparatus for athletes engaged in physical contact sports. It allows athletes to develop their maximum hitting force, and accustom themselves to the resultant counter blows. The athlete is fitted into an upper-body harness, fastened by a tether to a shock absorbing spring assembly, which is fastened to a fixed post, weighted bag, or another athlete. The athlete then runs to the end of the tether and is forcefully stopped.

5 Claims, 13 Drawing Figures

INVENTOR
RICHARD E. THATCHER

FIG. 6
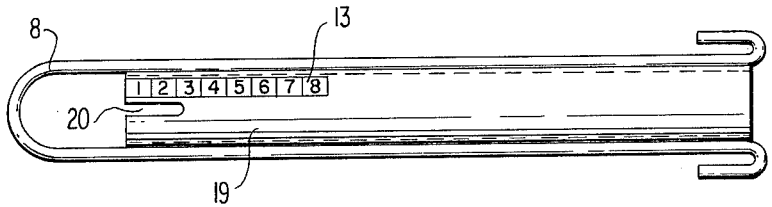
FIG. 7
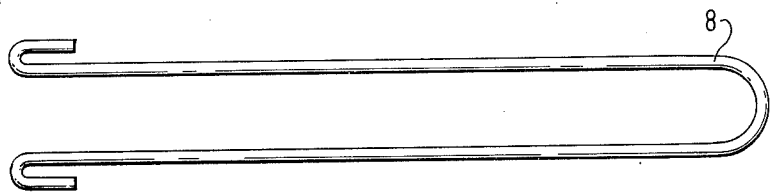
FIG. 8
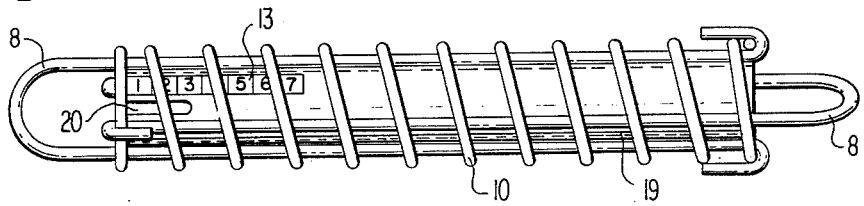
INVENTOR
*RICHARD E. THATCHER*
FIG. 9
FORCE = $(1/2)(W/g)(V)^2 = (1/2)(128.8/32.2)(V)^2$
FORCE = $2V^2$
| VELOCITY MILES/HOUR | VELOCITY FEET/SECOND | (VELOCITY)² FEET-SECOND² | FORCE FOOT-POUNDS |
|---|---|---|---|
| 3.5 | 5 | 25 | 50 |
| 7.0 | 10 | 100 | 200 |
| 10.5 | 15 | 225 | 450 |
| 14.0 | 20 | 400 | 800 |
| 17.5 | 25 | 625 | 1250 |
| 21.0 | 30 | 900 | 1800 |

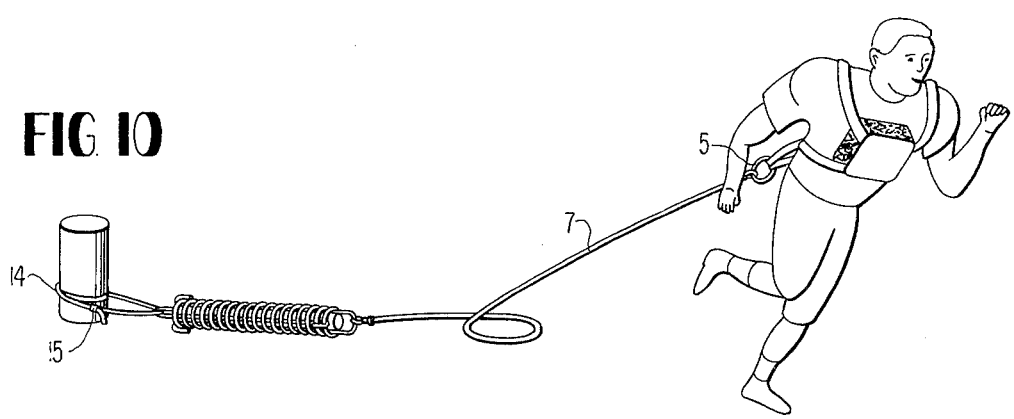
FIG. 10
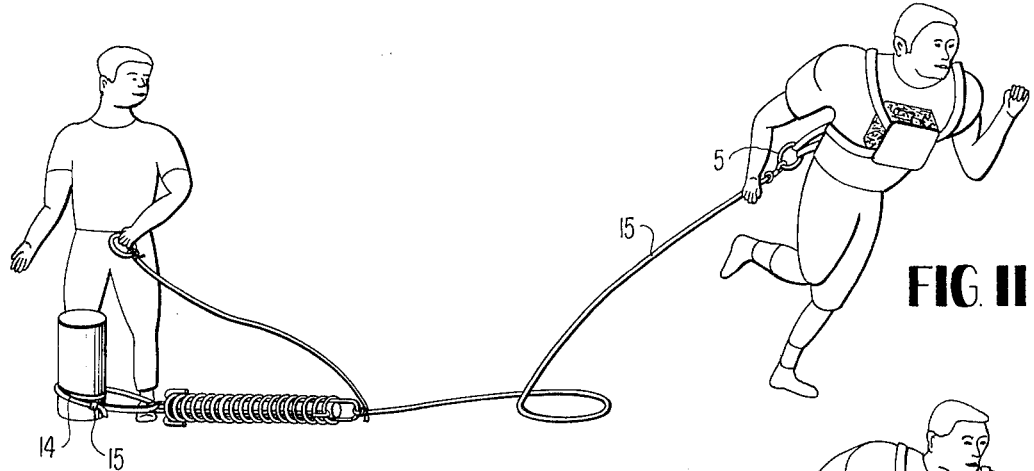
FIG. 11
FIG. 12
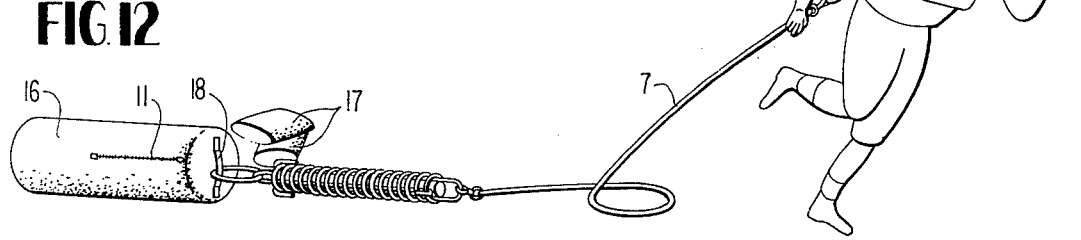
INVENTOR
RICHARD E. THATCHER
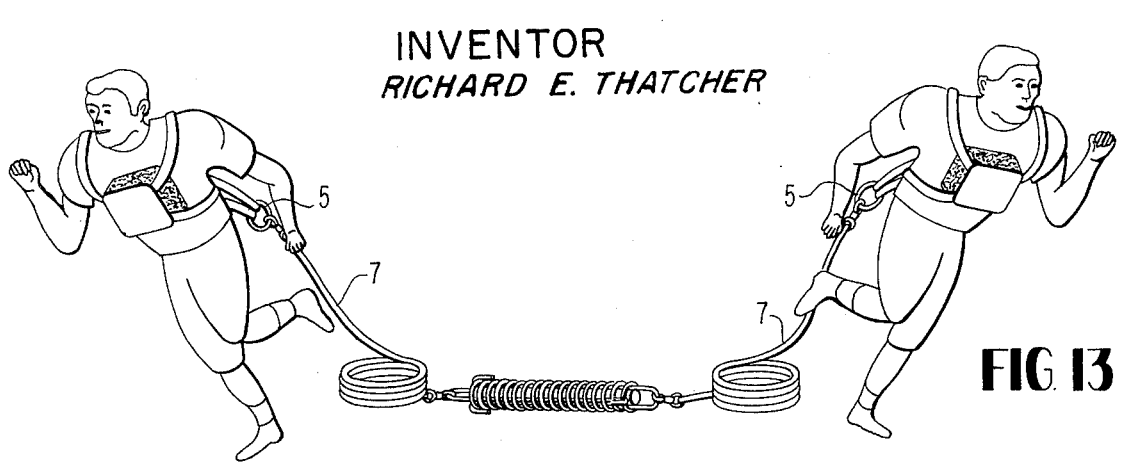
FIG. 13

PHYSICAL CONTACT TRAINING APPARATUS

BACKGROUND OF THE INVENTION

This invention relates to a physical conditioning apparatus required for the many various means of training athletes for contact sports, such as football, rugby, lacrosse, soccer, hockey and other contact sports.

Athletes, particularly football players, are required to physically contact and overcome an opponent, either by blocking, tackling, or running over their opponent. In learning to accomplish this, the athlete is subjected to much physical abuse, and, a high incidence of injury. However, the athlete must develop the ability to deliver his maximum hitting force, and to receive the resultant counter force. Therefore, the athlete must run against another athlete and hit into him, again, and again, in order for his body to develop driving power, balance, break-away ability, and a mental attitude that he can, and will, out hit and overcome his opponent, regardless of abuse.

Prior art apparatus, as an example, U.S. Pat. No. 3,519,269, Penny & Howlett, allows an athlete to run from a pull responsive tether, while being restrained by shoulder straps, requiring a second person regulating the tether. However this apparatus does not allow for a consistant controllable violent impact, nor is an athletes shoulders capable of safely absorbing such a force. Other prior art, U.S. Pat. No. 3,411,776, Hockesvick, again allows for a pull-responsive tether for exercising. Again U.S. Pat. No. 1,543,346 Titus, illustrates an exercise apparatus from a head harness, using a tether and weight extened over a pulley. Again U.S. Pat. No. 1,345,533, Chytracek illustrates a shock absorbing parachute harness strap, but is dissimilar to our use.

Other training devices such as, blocking sleds, which allows athletes to push against, and strike with their shoulders allow for limited impact conditioning, though effective for other much needed phases of conditioning.

The force a person can develop can be theoretically calculated by the equation: Force = $\frac{1}{2}mv^2$. The force he can develop is proportional to $\frac{1}{2}$ his mass, which is his weight divided by the gravity constant 32.2 lbs/sec$^2$, times the square of his velocity at the time of contact, or impact. The chart, FIG. 9 illustrates the theoretical force developed by a 128.8 pound athlete over his range of speed.

Often, athletes are capable of running 100 yards in 10 seconds, for convenience this figure will be used as the upper limit of speed for the athlete. This is equivalent to approximately 20.8 miles per hour, 10 yards per second, or 30 feet per second. To establish the chart with the force equation = $\frac{1}{2}mv^2$ we will use feet per second, also illustrating the approximating mile per hour, of which we are more familiar with.

It is evident from the chart, (FIG. 9) that the speed that an athlete attains at impact is very important, regardless of his weight. Provided he can deliver, and absorb the forces. Presently, most athletes learn to contact an opponent by running against each other. The physical abuse resulting from this manner of training often creates contact shy, injured athletes. Athletes often slow down to hit during conditioning, to survive. Resulting consequences are that the athletes body never becomes used to, nor develops strength, balance, or break-away ability.

Many established athletes must keep in top hitting form but cannot endure the contact training required. They compromise in training with less contact, and often tolerate some loss of ability.

It is therefore an object of this invention to provide a means of teaching the athlete the importance of speed in contact sports; of measuring his force developed; to condition his body for impact at the maximum speed he can attain over varying distances; to condition his body to achieve maximum force at impact and to sustain the driving force; to condition a pair of athletes competing against each other without contact, while achieving maximum force; to condition an athlete to achieve maximum force and develop the break-away running ability. Moreover, because of the apparatus design, the invention will accomplish the teaching, measuring, and conditioning, without requiring the athletes to physically contact each other. Thereby keeping physical abuse, and injury to a minimum.

In short, most prior art conditioning apparatus are not suitable in preparing an athlete, mentally, or physically to deliver his maximum hitting force, also receiving the resultant counter-force. Prior art apparatus cannot simulate the impact an athlete would receive at higher speeds without incurring physical abuse or injury.

SUMMARY OF THE INVENTION

The conditioning apparatus consist of an upper-body harness assembly, which is infinitely adjustable. A tether which is fastened to a draw spring assembly which provides a means of allowing adequate impact without undue shock, and a means of measuring the force imparted into the spring. The draw-spring assembly is fastened in a fixed position for one phase of training.

The athlete is fitted into the upper body harness and fastened with a tether to the fixed draw-spring assembly. He then runs away from the fixed draw spring, and is stopped as he reaches the end of the tether.

The upper-body harness is designed to impact, or "strike" the athlete in what is considered the best position to knock an opponent down. The force is imparted at the chest or breast bone, above his center of gravity, as shown in FIG. 1.

The upper body harness is designed to absorb the greater part of the impact force in the final wrap of the strap across the chest, and to keep this impact force away from the weaker shoulder joints, shoulder blades, collar bones, and ribs.

The harness consist of one length of strap, two circular rings, and a cloth front piece, which is used to guide the cross straps through sewn channels, and to house a foam cushion used to distribute the force over the breast.

The harness is made infinitely adjustable having no buckles or fasteners to adjust, in the following manner. The length of strap is passed through one ring, passing equal lengths of strap on each side. The ring is placed on the center of the upper-body back, then pass the straps over the shoulder, and cross in front across the chest. Place the straps through the sewn cross channels provided in the front piece, having the foam cushion between the chest and the straps. Then pass both straps under the athletes arms, and back to the ring on the back, up through the lower portion of the ring. Both these straps are then drawn through taking up all slack, and are then sewn to a second ring from which a tether is fastened to. The straps will tighten when pulled tight, and stay in the same relative position during any number of runs and stops. Or, the harness can be made with two equal lengths of strap, and sewn to this same back ring and made infinitely adjustable in the same aforementioned manner. The rings could also be of a different configuration, other than circular.

The tether consist of a woven rope, of adequate strength, having a safety type latch on each end, which is connected from the harness ring to the draw spring assembly draw rod.

Another tether used consist of a woven rope of adequate strength, having a safety type latch on one end only. The other free end is tied to the draw spring assembly draw rod, fashioned with a quick release slip-knot. This is used in a phase of training, whereas, the athlete runs against the a apparatus several time in succession, constantly attempting to break away. Another person stands at the draw spring assembly draw rod location and releases the slip knot, allowing the athlete to be unknowingly released without the impact the athlete is expecting. In this manner break-away balance and ability is developed. Many athletes will hit and contact an opponent, and rely on the opponents counter-force to keep the athlete from falling. If the opponent falls quickly the athlete often falls over the opponent. This phase conditions the athlete to maintain balance when the counter-force is suddenly removed, and to break away on his feet.

The shock absorbing part of the apparatus consist of a draw bar spring assembly. The springs used are designed such that athletes of different weight and ability, use springs which are designed with a spring rate most condusive to their present ability and weight.

Basically, an athlete who is learning to hit and be hit should start with a spring assembly which has a softer hit, or a lower spring rate. As the athlete progresses and learns to hit or be hit harder, the athlete would graduate to a harder spring, or a spring having a higher spring rate.

The draw spring assembly is used because it is considered fail-safe. In the event that the compression spring fractures, the draw rods would keep the assembly intact, and not propel a portion of the spring at the athletes. Tension springs can be used for this apparatus, but are considered unsafe.

The compression spring used allows for the application of a more accurate, and consistant force scale measurement.

The draw bar assembly is fastened to a rigid post, pole, or abutement with the use of an adjustable strap for two phases of conditioning.

We have mentioned various training and conditioning phases, or applications of teaching, measurement, and conditioning resulting from varied uses of this apparatus. FIG. 10 illustrates the primary application of an athlete conditioning himself to deliver and receive the force he can develop. The apparatus draw spring is fastened in a fixed position, and the athlete runs to the end of the tether and is "Hit" stopped. The athlete can work alone, or under supervision. FIG. 11 illustrates break-away conditioning, whereas the athlete continually runs against the harness to break free. A supervisor breaks the athlete free at random, when he least suspects it. FIG. 12 illustrates the means of conditioning used for an athlete to develop force delivery and sustain a driving force. This will illustrate that the harder he hits, the further the weighted object will move without relying on driving force. FIG. 13 illustrates the competitive use, that is, going against another athlete to further illustrate; that having athletes of equal weight, the athlete attaining the highest speed and balance will usually force the other athlete back.

All of the aforementioned applications can be achieved without physical abuse or injury often incurred when athletes have to physically contact each other to achieve the same conditioning.

The apparatus is so designed that it is light and compact and can be readily transported, be hand carried by an individual and used at home, or any place other than the training field or location.

BRIEF DESCRIPTION OF THE DRAWINGS

The foregoing and other objects, features and advantages will be apparent from the following more particular description of a preferred embodiment of the invention, as illustrated in the accompanying drawings in which reference characters refer to the same parts throughout the different views. The drawings are not necessarily to scale, emphases instead being placed upon illustrating the principles of the invention in a clear manner.

FIG. 4 is the rear view again, illustrating completion of the the harness assembly with the tether snapped on.

FIG. 6 is a plan view of a draw rod with the spring stabilizer tube and the measurement scale adhered along the viewing side.

FIG. 7 is a plan view of a draw rod.

FIG. 8 is a plan view of a draw spring assembly.

FIG. 9 is a chart illustrating the theoritical force developed by an athlete over a normal speed range.

FIG. 10 is a view in perspective of the training apparatus constructed in accordance with the principles of the invention and illustrating how it is used for one phase of training.

FIG. 11 is a view, as in FIG. 10, further illustrating breakaway training.

FIG. 12 is a view as in FIG. 10, further illustrating sustained contact and driving force training.

FIG. 13 is a view, as in FIG. 10, further illustrating competitive use in training.

DESCRIPTION OF A PREFERRED EMBODIMENT

The aforementioned upper-body harness consist of the following pieces, and is assembled in the foregoing manner.

Figure 1:
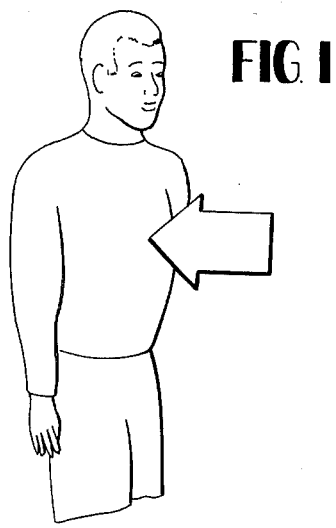
FIG. 1 is a view of a figure illustrating where the impact is imparted to the athlete.
Figure 2:
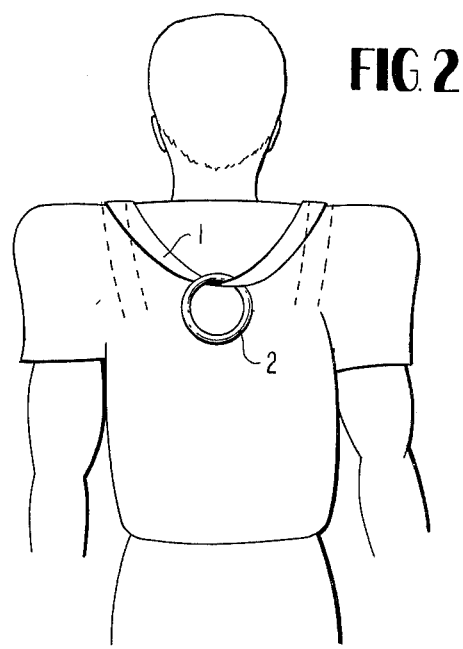
FIG. 2 is a view of the back of the athlete illustrating the starting assembly of the harness.
Figure 3:
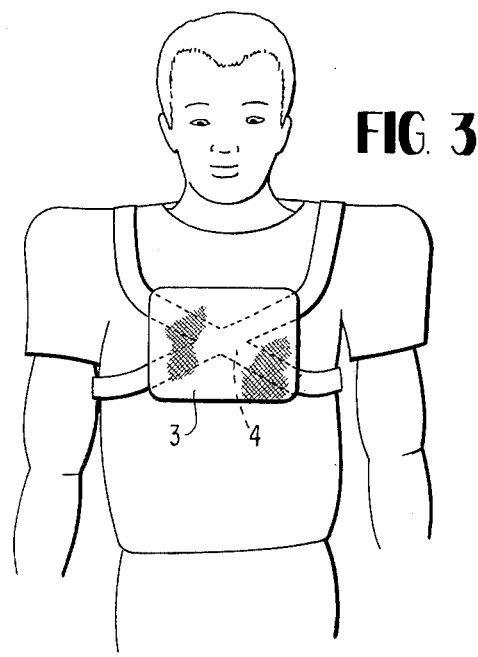
FIG. 3 is a front view of the same, illustrating location of breast pad and strap guide.
Figure 4:
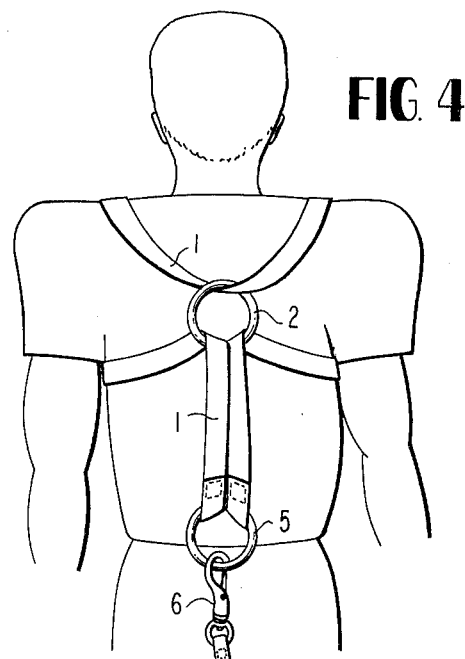
Figure 5:
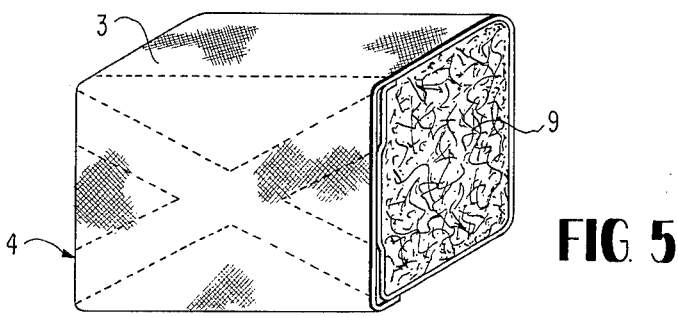
FIG. 5 is a front view of the breast pad and strap guide assembly.

Referring to the drawings and more particularly to FIG. 2, a circular ring 2 referred to as the back-harness ring is placed on the center-back of the torso and the length of strap 1 are then passed through the back-harness ring 2 in fashion shown. The straps 1 are then passed over the shoulders to the front breast and crossed as shown in FIG. 3. The breast pad 3 is placed on the breast having the sewn channels 4 outward. The straps 1 are then passed through the sewn cross channels 4 in the breast pad 3, and are then passed back under the arms to the back of the torso, as shown in FIG. 4. The straps 1 are then passed back through the lower portion of the back harness ring 2. The straps 1 are then drawn up to even lengths, taking up all the slack in the upper-body harness. The straps 1 are then passed through the second circular ring, referred to as the tether ring, 5 and sewn in and adequate fashion.

The aforementioned tether 7 consist of a length of woven rope having a safety type latch 6 on both ends for connecting the tether ring 5 to the draw rod 8, which is part of the draw spring assembly, in FIG. 8. Another tether 15 used consist of a woven rope of adequate strength, having a safety type latch 6 on one end and one free end. Other tethers 7 of cable, straps, rope could also be used. However, woven rope is preferable.

The aforementioned breast pad 3 consist of a durable cloth of adequate strength, constructed and sewn in a fashion to allow the straps 1 to be guided and passed through the sewn channels 4 and to house a foam pad 9. The foam pad is worn between the straps and the breast, to distribute the impact force from the upper-body harness evenly across the breast.

The aforementioned draw-spring assembly, FIG. 8, consist of one draw rod 8 having a spring stabilizer tube 19 welded inside the drawrod shafts. The stabilizer tube 19 prevents the compression spring 10 from collasping during deflection. The slot 20 is provided to allow for ease of assembly of the second draw rod 8 when inserted into the compression spring 10. The tube 19 is welded in a position between the draw rod 8 shaft to as to allow the measurement scale 13 mounted on the tube 19 to be in the same linear position as the compression spring will be in draw spring assembly FIG. 8. The measurement scale 13, preferable of a bright pre-printed durable adhesive backed material is adhered onto the stabilizer tube 19 outer wall. Embossing, etching, or painted measurement graduations could also be used. The various compression springs 10 use, are designed and selected as having various spring rates condusive to absorbing the forces developed by athletes, ranging from the small minor beginner, to the professional. The springs used are calibrated in a standard manner. That is, the force required to compress the spring from its full length to closed height is plotted, and recorded. A chart is provided for each spring 10 indicating the force required to compress each spring over its range. A corresponding chart, correlating the measurement scale 13 on the spring stabilizer tube 19 is made up to provide a related corresponding force measurement reading. The deflection imparted into the spring is two times the indication on the measurement scale 13 on the spring stabilizer tube 19, due to the manner in which a draw spring functions. That is, the spring 10 is compressed an equal length from each end.

In FIG. 10, an adjustable strap 14 of adequate strength are made up of an adjustable buckle 15 of adequate strength and are used to provide a means to anchor the apparatus to a fixed position. FIG. 11 also illustrates the use of the same adjustable strap 14 & 15 assembly.

FIG. 12 illustrates the application of a weighted bag 16, in which weighted increments 17 are preferably, sand filled plastic bags of adequate strength, so as not to split during handling and use. The weighted bag 16 can be a standard military duffel bag, or made up to suit. It should have a strap 18 attached to the bag in a fashion and suitable for the rigorous use intended. It should have an easily open and closing end for adding to, or, removing weights. A block of wood, weighted sled, or other weight carrying means could also be used in place of a bag.

The apparatus used in this invention is not only effective but it is inexpensive and practical. The harness assembly used is inexpensive and is easy to make, repair, or replace. The draw spring assemblies are easily obtained, and are durable. The weighted bag with its sand filled bags are simple an readily available. The entire apparatus assembly, that is, harness, draw spring, and tether can be placed in the weighted bag, and readily transported, or stored. The sand filled plastic bags can be left out.

While the invention has been particularly shown and described with reference to a preferred embodiment, it will be understood by those skilled in the art that various changes in form and detail may be made therein without departing from the spirit and scope of the invention.

The embodiment of the invention in which an exclusive property or privilege is claimed are defined as follows:

1. A teaching and conditioning apparatus to be used by a person such as an athlete comprising an adjustable upper-body harness attachably associated by means of a tether to a draw spring assembly, and means for measuring force imparted to same, said harness comprising two essentially equal lengths of strap which at one end are joined and at the other end engaged with a ring, said straps being held in crossed juxtaposition by channel guide means slideably positionable on said straps between said joined end and said ring, said straps being adapted to pass through said ring at a lower portion thereof so as to form an upper pair of loops and lower pair of loops, said upper pair of loops, extending from the ring to the channel guide means, being adapted to accomodate the shoulders of the athlete and said lower pair of loops, extending from the channel guide means to said lower portion of said ring, being designed to extend from the chest, around the side and to the back of the athlete, said loops being simultaneously tightenable by tension applied from the direction of said joined end, said draw spring assembly comprising a coil spring and at least two opposing draw rods positioned within same, said draw rods engaging each end of the spring in a manner such that opposing force applied to the draw rods causes restorable compressive displacement of said spring, and means associated with said draw spring assembly for measuring the extent of said displacement, said draw spring assembly being attachable at one draw rod to a tether extending to the joined end of the straps of said harness, and being attachable at an opposing draw rod to a means for resisting motion of the athlete.

2. Apparatus of claim 1 wherein said two lengths of strap belong to a single integral strap which, at substantially its midpoint, slideably passes through and wraps around said ring.

3. Apparatus of claim 1 wherein cushion means are associated with said channel guide means to distribute force over the chest of the athlete.

4. Apparatus of claim 1 wherein said upper body harness is infinitely adjustable to the athlete by tensioning force exerted at the joined end of said straps.

5. Apparatus of claim 1 wherein said means for resisting motion of the athlete comprises a weight carrying means.

* * * * *